United States Patent [19]
Resk et al.

[11] Patent Number: 5,588,834
[45] Date of Patent: Dec. 31, 1996

[54] SYSTEM FOR COLOR MATCHING A DENTAL PROSTHESIS

[76] Inventors: Richard E. Resk, 85-14 158th Ave., Howard Beach, N.Y. 11414; Jeffrey R. Shapiro, 35 Liberty St. #19C, New York, N.Y. 10005; Daniel Materdomini, P.O. Box 781, Woodland Hills, Calif. 91365

[21] Appl. No.: 444,150

[22] Filed: May 18, 1995

[51] Int. Cl.⁶ .............................. A61C 19/10; A61C 5/08
[52] U.S. Cl. .............................. 433/26; 433/218
[58] Field of Search ........................ 433/26, 218

[56] References Cited

U.S. PATENT DOCUMENTS

| | | | |
|---|---|---|---|
| 3,507,042 | 4/1970 | Hana | 433/26 |
| 3,964,167 | 6/1976 | Yerkes | 433/26 |
| 4,810,193 | 3/1989 | Wieder | 433/26 |
| 5,004,417 | 4/1991 | Giaramita | 433/26 |
| 5,240,414 | 8/1993 | Thompson | 433/26 |
| 5,257,931 | 11/1993 | Pozzi | 433/26 |
| 5,261,815 | 11/1993 | Pozzi | 433/26 |

*Primary Examiner*—Nicholas D. Lucchesi
*Attorney, Agent, or Firm*—Gottlieb, Rackman & Reisman, P.C.

[57] ABSTRACT

A system for color matching a dental prosthesis is provided. The system includes a shade guide or color range finder comprising a plurality of color elements, each of which identifies a different color than the remaining elements. This system also includes a plurality of plastic shells that are configured for placement on or along side a patient's anterior or posterior tooth that has previously been prepared for receiving a dental prosthesis. The shells correspond in color to the colors of the color range finder elements. The system further includes some type of coloring for selectively modifying the aesthetic appearance of a shell so that the dental practitioner can prepare an accurate representation of what is to be produced as a dental prosthesis in the laboratory.

15 Claims, 3 Drawing Sheets

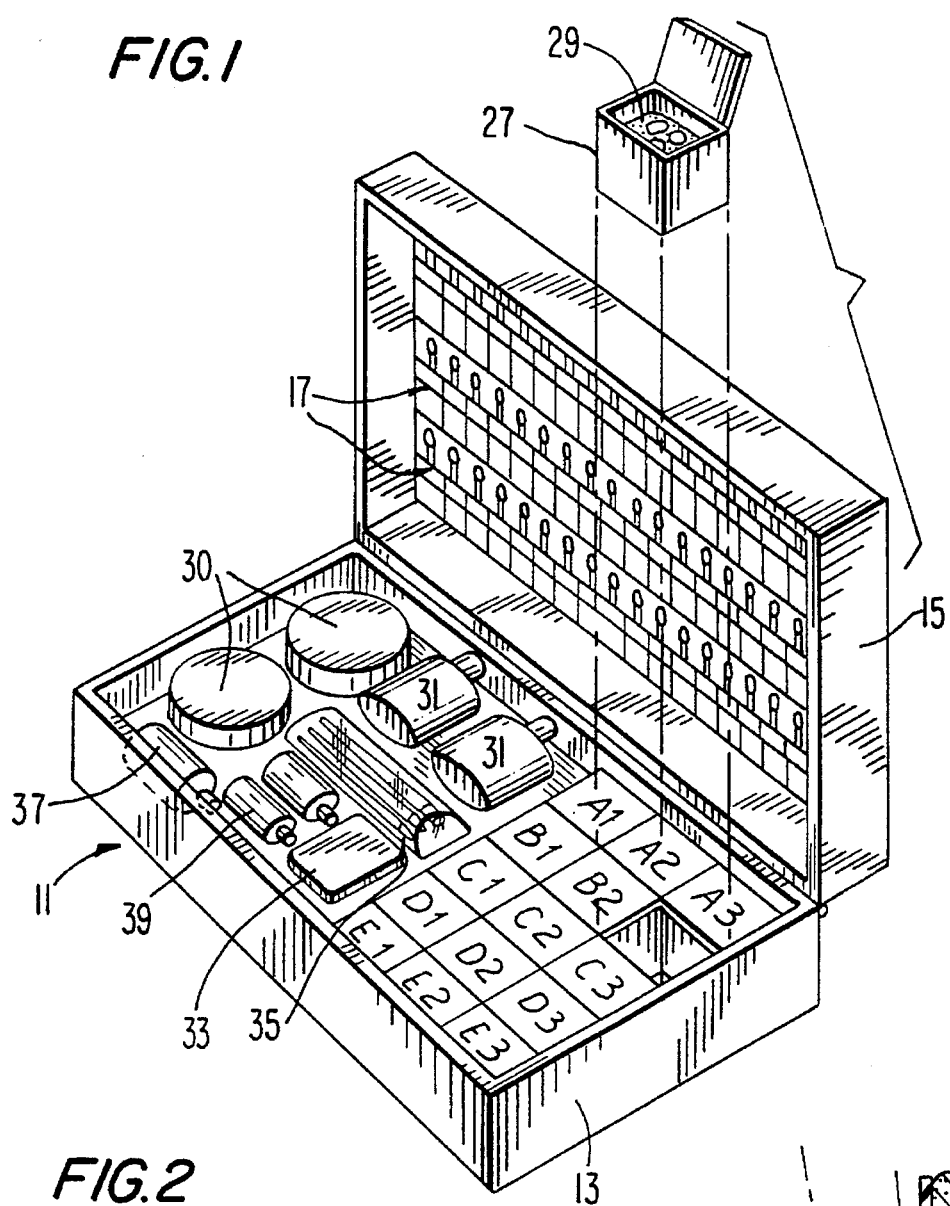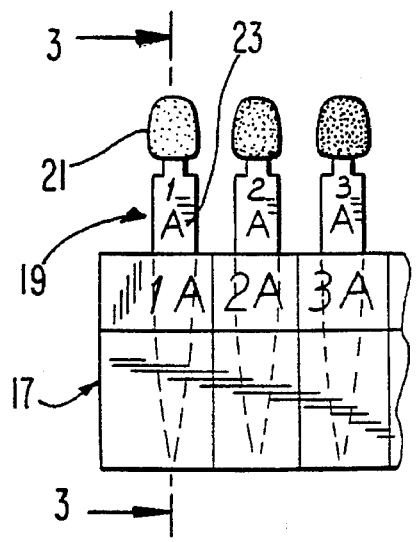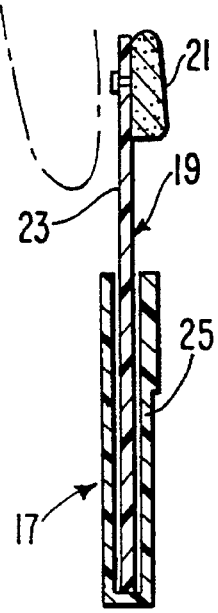

SYSTEM FOR COLOR MATCHING A DENTAL PROSTHESIS

BACKGROUND OF THE INVENTION

This invention relates to the fabrication of prosthetic teeth such as crowns and bridges, and more particularly to color matching a prosthetic tooth through the patient's dentition.

Presently, dentists and dental practitioners use dental shade guides in order to accomplish color matching for fabricated dental prosthetic teeth. Shade guides used today were originally intended for the selection of commercially manufactured high temperature vacuum-fired porcelain teeth for dentures. The introduction of modern porcelain-fused-to metal ceramics led to the expansion of use of these guides to crown and bridge prosthetics.

Teeth on shade guides are typically made of material other than the actual porcelain-fused-to metal dental ceramic powder. Therefore, shade guide teeth contain different components and different color pigments than dental ceramic powders. Furthermore, such shade guide teeth are unrealistically thick and provide a different impression of color than ceramic fired to a metal base.

In addition, a conventional dental shade guide is less than satisfactory, since the dental practitioner cannot preview the final shade or color in relation to the natural dentition before sending impressions and/or color samples to the laboratory technician for preparation of the dental prosthesis. Moreover, the teeth of shade guides are not a true representation of a produced prosthesis due to material discrepancies between the prosthesis and the shade guide. Accordingly, conventional dental shade guides have been less than satisfactory as a color matching system for the preparation of dental prosthetics.

SUMMARY OF THE INVENTION

Generally speaking, in accordance with the invention, a system for color matching a dental prosthesis is provided. The system includes a shade guide or color range finder comprising a plurality of color elements, each of which identifies a different color than the remaining elements. This system also includes a plurality of plastic shells that are configured for placement on a patient's tooth that has previously been prepared for receiving a dental prosthesis. The shells correspond in color to the colors of the color range finder elements. The system further includes some type of coloring means for selectively modifying the aesthetic appearance of a shell so that the dental practitioner can prepare an accurate representation of what is to be produced as a dental prosthesis in the laboratory.

In using the system, the dental practitioner selects a color element from the color range finder that is the closest in color to the tooth to which a dental prosthesis is to be applied. This is typically achieved by placing one or more of the color elements of the range finder directly next to or over the desired tooth to see which color is the closest. Once a particular color element has been selected, the dental practitioner then selects a plastic shell that corresponds in color to the color of the selected range finder color element. This shell is placed over or on the tooth where various colorants are painted thereon to modify the aesthetic appearance of the shell in order that it is a virtual exact match in color to the tooth. Once coloring of the shell has been completed, the shell may be removed from the tooth and then sent to the dental lab for preparation of the dental prosthesis. Since the lab has a far more accurate color representation of the tooth to which the prosthesis is to be applied, a far more color accurate prosthesis can be created.

Accordingly, it is an object of the invention to provide an improved system for color matching a dental prosthesis.

Still another object of the invention is to provide a dental color matching system which aids the dentist and dental practitioner in selecting a tooth shade for a prosthesis that meets the aesthetic expectations of a patient.

Yet a further object of the invention is to provide a color matching system for a dental prosthesis by which the dentist or dental practitioner is able to precisely record color of a patient's remaining dentition.

A further object to the invention is to provide a color matching system for a dental prosthesis that is suitable for both anterior and posterior tooth forms.

Still other objects and advantages of the invention will in part be obvious and will in part be apparent from the following description.

The invention accordingly comprises the features, properties and relation of elements which will exemplify the system hereinafter described, and the scope of the invention will be indicated in the claims.

BRIEF DESCRIPTION OF THE DRAWINGS

For a fuller understanding of the invention, reference is made to the following description, taken in connection with the accompanying drawings, in which:

FIG. 1 is a perspective view of a kit for the inventive dental prosthetic color matching system;

FIG. 2 is a top plan view of a portion of the anterior tooth color range finder of the inventive color matching system;

FIG. 3 is a cross-sectional view taken along line 3—3 of FIG. 2;

DETAILED DESCRIPTION OF THE PREFERRED EMBODIMENTS

Figure 4:
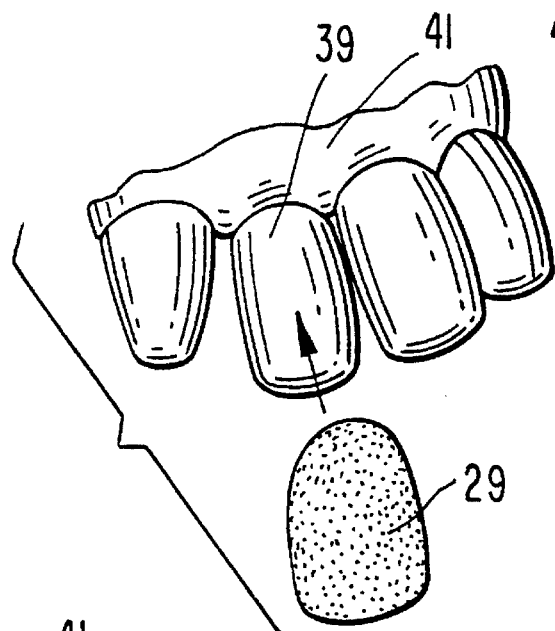
FIG. 4 is a front elevational view showing a plastic shell of the inventive system being placed over a selected anterior tooth of a patient.

Referring first to FIG. 1, a dental kit generally indicated at 11 that is used in the inventive system is shown. Kit 11 comprises a bottom container 13 and a hinged cover 15. Cover 15 houses a series of color range finders 17 that are suitable for the anterior teeth of a patient, as is well known in the art, comprising a plurality of color elements 19.

Color elements 19 of color range finder 17, as best shown in FIGS. 2 and 3, comprise a head 21 in the shape of a tooth, and a stem 23 depending therefrom. Head 21 of each of color elements 19 is made of a dental ceramic material such as acrylic, composite derivatives or resins, as well known in the art. Each of heads 21 of elements 19 has a different color or hue than the remaining heads of elements 19 in shade guide 17. In other words, and referring to FIG. 2, head 21 of the color element designated 1A has a slightly different hue than head 21 of the color element designated 2A. Similarly, head 21 of the color element designated 3A has a different hue than the hue of heads 21 of the first two color elements. Thus, shade guide 17 provides a spectrum of true colors which can be used in matching one of the elements (by color) to the desired patient's tooth, as described hereinafter.

Referring once again to FIG. 1, container 13 of kit 11 includes a plurality of boxes 27, each including a written designation such as A1, A2, etc. Each of boxes 27 contains a series of shells 29 which, as described below, are used in the color matching system of the invention. Moreover, as discussed in greater detail, each of color elements 19 of range finder 17 has a corresponding box 27 which contains shells 29 of an identical color or hue as the color or hue of head 21 of element 19.

On the left side of container 13 of kit 11, there is provided a pair of containers 30 for holding a plurality of color modifiers housed in a series of vials (not shown). Typically, at least 15 different coloring modifiers are included in a kit so that different shades can be selectively painted on a shell, as discussed below. Each color modifier is derived from the primary colors.

The color modifiers consist of a formulation which can be mixed together in appropriate proportions to obtain a wide range of colors needed to imitate the stains on teeth and which will cure in a few seconds under a dental curing lamp. The formulations are made up of acrylic monomers and/or polymers, preferably di- and tri-functional in the acrylic groups, such as BIS-GMA and diethylene glycol, thickened and reinforced with mineral fillers such as acid washed silica (silicon dioxide) and sub micron silica, photosensitive curing agents such as Irgacure 651, Quantacure BEA, etc. and other light curing agents known to those familiar with the art, and various non-toxic colorants, such as titanium dioxide, ferric oxide, chromium compounds, phthalocyanine dyes, etc., in suitable proportion. Instead of using a light curing agent, a self-curing agent may be substituted, as is well known in the art.

Kit 11 also includes a pair of bottles 31 for containing surface priming material, a palate 33 for mixing the color modifiers, a plurality of brushes 35 which are used for applying the color modifiers on shells 29, a bottle 37 for containing a diluting agent, and a bottle 39 for containing a sealing agent.

Turning now to FIG. 3, use of range finder 17 is now described. Range finder 17 is placed adjacent to the patient's mouth such that a comparison can be made between the color of head 21 of element 19 and the selected anterior tooth 39. When a desired color match is achieved, for example color element 1A, a corresponding box 27 of kit 11, namely box A1, is retrieved and a plastic shell found therein is selected.

Figure 5:
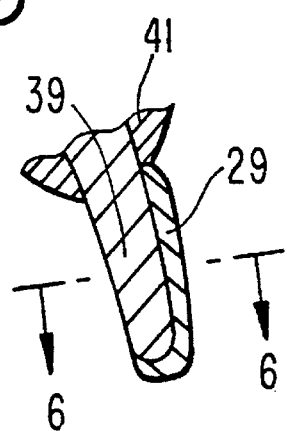
FIG. 5 is a cross-sectional view showing the shell in FIG. 4 placed over the patient's anterior tooth.
Figure 6:
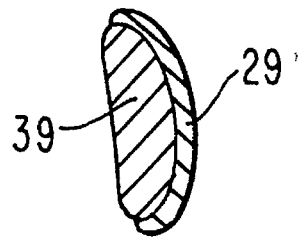
FIG. 6 is a cross-sectional view taken along line 6—6 of FIG. 5.

As shown in FIGS. 4–6, plastic shell 29 is placed over anterior tooth 39. Then the dental practitioner, in accordance with the invention, and in order to create an aesthetic appearance of the shell which blends in perfectly with adjacent anterior teeth, uses the color modifiers provided in container 30 of kit 11 in order to modify the shell color. Specifically, the shell is painted using selected light or non-light cured color modifiers, utilizing one of brushes 35. To facilitate use of the system by the dental practitioner, kit 11 may include a set of instructions.

Before applying the selected color modifiers, the surface of the plastic shell shall be prepared for bonding. Depending on the exact material that the shell is composed of, it may be only necessary or desirable to wipe the surface with isopropyl alcohol or acetone, or a cleaning and drying agent such as described in U.S. Pat. No. 3,905,110, or to sand the surface, so as to remove oils or greases or other surface contamination, for the color modifiers to bond well. In other cases, it may be desirable to apply a surface priming material, either a solvent-drying varnish, or a two-component catalytic cure coating of epoxy resin, or polyurethane resin, for example, or alkyl-2-cyanoacrylate monomer systems, such as ethyl-2-cyanoacrylate. This is a fast setting, single container material providing good bonding strength to a wide variety of plastic materials, and which has great ease of use. The primer materials are housed in bottles 31. Moreover, when using the type of shells generally used in dentistry, the color modifiers of the type described bond adequately to the shell directly, or to it once it has been wiped with a solvent and/or sanded lightly.

The color modifiers are generally contemplated for use directly as supplied. However, a diluting agent may also be used to dilute one or more of the selected color modifiers prior to application to the shell in order to modify the application more to the dentist's preference, or to improve the adhesion to the shell. The diluting agent is stored in bottle 32 of kit 11, and may be selected from solvents such as acetone or isopropyl alcohol, or may be methacrylate monomers such as methylmethacrylate, ethyl methacrylate, or diethylene glycol dimethacryle or blends of such monomers and suitable catalysts such as covered in U.S. Pat. No. 3,730,947 or 3,751,399.

A sealing agent may also be applied to the shell once the selected color modifiers have been painted on in order to seal the color on the shell and enhance the gloss. The sealing agent is stored in bottle 39 of kit 11 and may be chosen from the classes of clear air-dry coatings such as cellulose nitrate lacquers or ester varnishes. It is especially useful to use an alkyl-2-cyanoacrylate brush-on coating such as Lee "cyanoacrylate gel" coatings, based on such monomers, as it is easy to apply or brush-on such systems, and since they improve the overall product, since the acrylic-based color modifiers may have some surface tack (due to oxygen inhibition) and these coatings seal off oxygen and copolymerize with the surface of the color modifier.

Once shell 29 has been painted to the practitioner's satisfaction, it is then removed and sent to the dental laboratory. Since shell 29 provides a far more accurate representation of the color and appearance of what the dental prosthesis should be, the dental lab can produce a prosthesis that has a coloring and appearance that is far more satisfactory than achieved in prior art systems.

Figure 7:
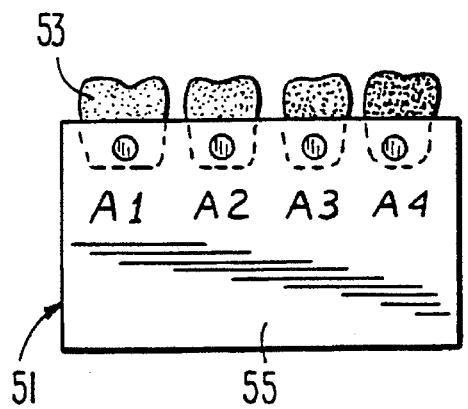
FIG. 7 is a front elevational view of a posterior tooth color range finder.
Figure 8:
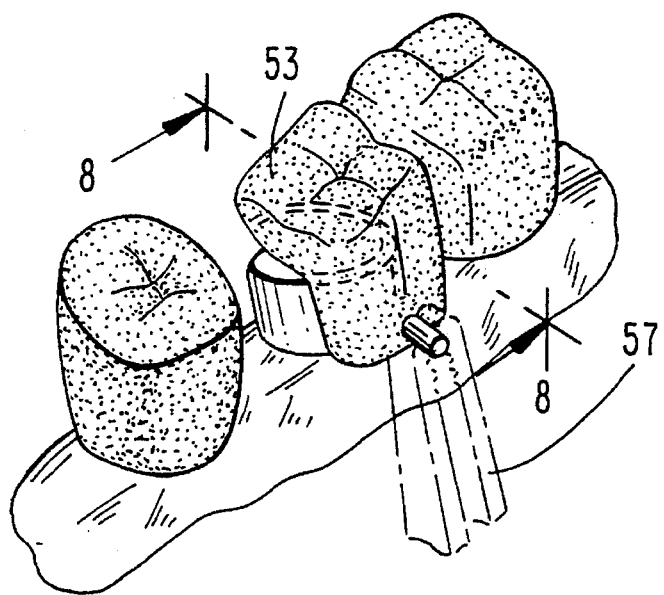
FIG. 8 is a perspective view showing application of a color element from the color range finder of FIG. 7 to a posterior tooth.
Figure 9:
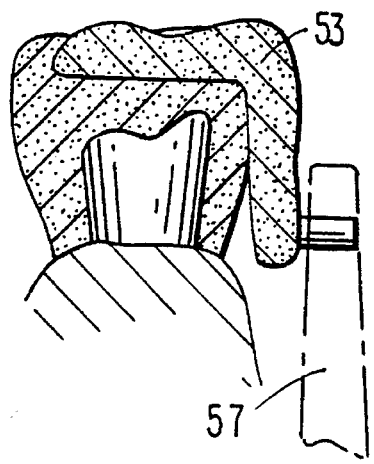
FIG. 9 is a cross-sectional view taken along lines 9—9 of FIG. 8.

Turning now to FIG. 7, there is provided a second color range finder suitable for a patient's posterior teeth and generally indicated at 51. Range finder 51 comprises a series of head elements 53, each of which identifies a different color than the remaining elements. Elements 53 are fixed in a row along a stand 55. In use, range finder 51 is placed over the area of a patient's mouth to which a prosthesis will be applied in order to determine which element 53 provides the most accurate color match. Alternatively, utilizing an arm 57, as best shown in FIGS. 8 and 9, each of elements 53 may be placed in the desired location in the posterior portion of a patient's mouth to determine which element 53 is most appropriate.

Figure 10:
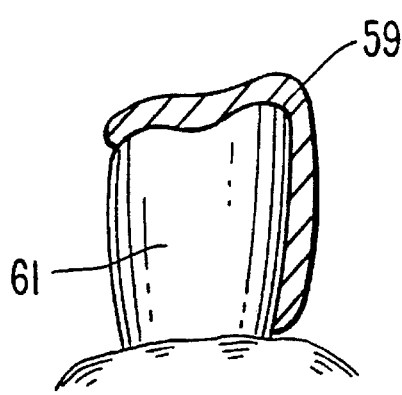
FIG. 10 is a cross-sectional view showing placement of a second shell of the inventive system over a posterior bicuspid tooth.
Figure 11:
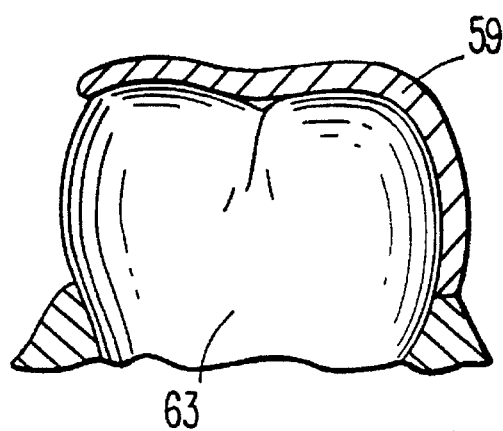
FIG. 11 shows placement of a third shell over a posterior molar tooth of a patient.

Once a specific tooth member 53 of range finder 51 has been selected, such as the tooth member designated A1, a corresponding shell 59, as shown in FIG. 10, and that has a structure that is suitable for placement over a patient's posterior bicuspid, is selected. Selected shell 59 is placed over posterior tooth 61 in the patient's mouth (see FIG. 10) where it is painted by the dental practitioner, as previously described, in order to achieve a customized plastic shell that accurately represents the color that is needed for the dental prosthesis. Alternatively, as shown in FIG. 11, shell 29 may be placed over a posterior molar tooth 63. Once painting of the shell has been completed, as before, it is sent to a dental laboratory, for production of the prosthesis.

It will thus be seen that the objects set forth above, among those made apparent from the preceding description, are efficiently attained, and, since certain changes may be made in carrying out the above process and in the system set forth set forth, without departing from the spirit and scope of the invention, it is intended that all matter contained in the above description and shown in the drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A system for customized color matching of a dental prosthesis comprising:

a color range finder comprising a plurality of color elements, each of said elements identifying a different color than the remaining elements;

a plurality of shells comprising individual shell groups, the shells of each of said group specially designed and anatomically configured for selective direct placement intimately over a specific anterior or posterior tooth that has been prepared for receiving said dental prosthesis, at least one of said specially designed and anatomically configured shells in each shell group corresponding in color to the basic color of each of said range finder elements; and means for selectively coloring a selected shell.

2. The system of claim 1, wherein each of said elements comprise a head for identifying said different colors.

3. The system of claim 1, wherein the coloring means comprises at least one color modifier.

4. The system of claim 3, wherein said at least one color modifier includes a colorant, a light curing material, a self curing material and an organic monomer or polymer.

5. The system of claim 3, wherein said coloring means further comprises a surface priming material.

6. The system of claim 3, wherein said coloring means further comprises a diluting agent.

7. The system of claim 3, wherein said coloring means further comprises a sealing agent.

8. The system of claim 1, further including means for selectively applying said coloring means to said selected shell.

9. The system of claim 8, wherein said applying means comprises a brush.

10. The system of claim 8, further including means for mixing said coloring means.

11. A method for customized color matching of a dental prosthesis comprising:

identifying a color element of a color range finder whose color is closest to a patient's anterior or posterior tooth that has been prepared for receiving a dental prosthesis;

selecting a shell from a group of shells that is specially designed and anatomically configured for placement directly over said prepared tooth and that corresponds in color to the basic color of said selected range finder element;

placing said selected shell intimately over said patient's tooth that has been prepared for receiving said dental prosthesis;

coloring said placed shell so that its aesthetic appearance is what the practitioner desires; and providing said colored shell to a dental laboratory for preparation of the prosthesis.

12. The method of claim 11, further comprising the step of applying a surface primer to said shell prior to said coloring step.

13. The method of claim 11, further comprising the step of applying a sealing agent to said shell after said coloring step and prior to said providing step.

14. The method of claim 11, wherein said coloring step comprises applying a color modifier to said shell selected from the group consisting of a light-cured modifier and a self-cured modifier.

15. The method of claim 14, further comprising the step of diluting said color modifier prior to application to said shell.

* * * * *